US012599325B2

(12) United States Patent　　　　　(10) Patent No.:　US 12,599,325 B2

Jang　　　　　　　　　　　　　　　　　(45) Date of Patent:　　Apr. 14, 2026

(54) PSYCHOLOGICAL ANALYSIS APPLICATION AND PSYCHOLOGICAL ANALYSIS METHOD

(71) Applicant: UCARETRON INC., Anyang-si (KR)

(72) Inventor: Jee Hwan Jang, Hwaseong-si (KR)

(73) Assignee: UCARETRON INC., Anyang-si (KR)

( * ) Notice: Subject to any disclaimer, the term of this patent is extended or adjusted under 35 U.S.C. 154(b) by 260 days.

(21) Appl. No.: 18/568,853

(22) PCT Filed: Jun. 10, 2022

(86) PCT No.: PCT/KR2022/008224

§ 371 (c)(1),
(2) Date: Dec. 11, 2023

(87) PCT Pub. No.: WO2022/260475

PCT Pub. Date: Dec. 15, 2022

(65) Prior Publication Data

US 2024/0277272 A1　　　Aug. 22, 2024

(30) Foreign Application Priority Data

Jun. 11, 2021　　(KR) ........................ 10-2021-0076327

(51) Int. Cl.
　　　*A61B 5/16*　　　　　(2006.01)
　　　*A61B 5/11*　　　　　(2006.01)
　　　*G06F 3/04883*　　　(2022.01)
(52) U.S. Cl.
　　　CPC ............ *A61B 5/165* (2013.01); *A61B 5/1124* (2013.01); *A61B 5/162* (2013.01); *G06F 3/04883* (2013.01)

(58) Field of Classification Search
None
See application file for complete search history.

(56) References Cited

U.S. PATENT DOCUMENTS

| | | | |
|---|---|---|---|
| 2019/0200915 A1* | 7/2019 | Baker | .................. A61B 5/4839 |
| 2022/0125360 A1 | 4/2022 | Kim | |
| 2022/0280086 A1* | 9/2022 | Ryu | ....................... G16H 50/20 |

FOREIGN PATENT DOCUMENTS

| | | |
|---|---|---|
| CN | 110391019 A | 10/2019 |
| KR | 10-0750871 B1 | 8/2007 |
| KR | 10-2017-0132964 A | 12/2017 |
| KR | 10-1926836 B1 | 12/2018 |
| KR | 10-1998037 B1 | 7/2019 |
| KR | 10-2241804 B1 | 4/2021 |

OTHER PUBLICATIONS

International Search Report of PCT/KR2022/008224 mailed Nov. 21, 2022 from Korean Intellectual Property Office.

* cited by examiner

*Primary Examiner* — Michael W Kahelin
(74) *Attorney, Agent, or Firm* — Revolution IP, PLLC

(57) ABSTRACT

The present invention relates to a psychological analysis application including an input part having a screen adapted to receive a doodle or drawing from a user, an AI analysis module for analyzing the user's psychological state through the doodle or drawing inputted to the input part, an output part for outputting the result analyzed through the AI analysis module to the user, and a controller for outputting an original image to the screen of the input part to allow the user to copy the original image.

5 Claims, 4 Drawing Sheets

200

(a)                    (b)

(c)                    (d)

400

410                    440                    430

Input part          Controller          Output part

AI image module          460

AI analysis module          420

AI treatment module          450

PSYCHOLOGICAL ANALYSIS APPLICATION AND PSYCHOLOGICAL ANALYSIS METHOD

TECHNICAL FIELD

The present invention relates to a psychological analysis application and a psychological analysis method, more specifically to a psychological analysis application and method that is capable of performing Artificial Intelligence (AI) analysis for a user's copy of an original image to execute the psychological analysis of the user.

BACKGROUND ART

According to World Health Organization, a global suicide rate over the past 45 years is increased by about 60% so that more than one million people die due to suicide every year and the number of people who attempt suicide is about 20 times higher than the number of people died by suicide. According to Korean Statistical Office, the number of people died by suicide increases steadily after 2000, and in 2010, 15,566 people die by suicide in Korea. The statistical value means the number of people who have died by suicide per 100,000 population die is 31. 2, which shows the highest suicide rate among OECD member countries, and further, the suicide rate increases most rapidly among OECD member countries, which causes serious social problems.

Among methods for checking the emotional states of individuals, psychological analysis methods through pictures are utilized diversely.

Prior art literature: Korean Patent No. 10-0750871

The above-mentioned Prior art literature relates to a 'Psychological symptom diagnosis system and method using picture' that analyzes a main color and/or balance of the picture to determine the psychological symptoms of a subject who draws the picture. In this case, the color of the picture as well as the size and position thereof is analyzed to determine the psychological symptoms of the subject, and to allow the system to receive the picture, the picture is scanned to allow the edge and color thereof to be recognized through image processing, and next, the recognized result is received and analyzed through a computer.

The picture itself is important in the psychological analysis using the picture, but there is a need to recognize and analysis various behaviors of the subject in a process where he or she draws the picture.

DISCLOSURE

Technical Problem

Accordingly, it is an object of the present invention to provide a psychological analysis application and method that is capable of performing AI analysis for a user's copy of an original image to execute the psychological analysis of the user.

Technical Solution

According to one aspect of the present invention, a psychological analysis application may include an input part having a screen adapted to receive a doodle or drawing from a user, an AI analysis module for analyzing the user's psychological state through the doodle or drawing inputted to the input part, an output part for outputting the result analyzed through the AI analysis module to the user, and a controller for outputting an original image to the screen of the input part to allow the user to copy the original image.

The controller may output the original image to the user's input screen and allow the original image to disappear after a given time.

The AI analysis module may analyze the user's reaction time while he or she is copying the original image, a degree of an overlap between the user's drawing and the original image, and the shape of the user's drawing.

The AI analysis module may further include an AI treatment module for finding a treatment for the user's psychological state analyzed therethrough.

The controller may allow the treatment found through the AI treatment module to be outputted through the output part.

According to another aspect of the present invention, a psychological analysis application may include an input part having a screen adapted to receive a doodle or drawing from a user, an AI image module for analyzing the doodle or drawing inputted to the input part to produce a new image based on learned images, an AI analysis module for analyzing the user's psychological state according to the shape and color of the new image, an output part for outputting feedbacks for the new image produced through the AI image module and the user's psychological state analyzed in the AI analysis module, and a controller for controlling the displays of the input part and the output part.

The AI analysis module may further include an AI treatment module for finding a treatment for the user's psychological state analyzed therethrough and the controller may allow the treatment found through the AI treatment module to be outputted through the output part.

According to yet another aspect of the present invention, a psychological analysis method may include the steps of displaying an original image on a screen, receiving a user's copy of the original image, performing AI analysis for the user's psychological state according to the received user's copy of the original image, and outputting the user's psychological state analyzed.

The psychological analysis method may further include the step of: finding a treatment for the user's psychological state analyzed in the AI analysis step, so that the treatment found may be outputted in the output step.

Advantageous Effects of Invention

According to the present invention, the psychological analysis application and method performs the AI analysis for the user's copy of the original image to execute the psychological analysis for the user.

MODE FOR INVENTION

Hereinafter, the present invention will be described in detail with reference to the accompanying drawings.

Figure 1:
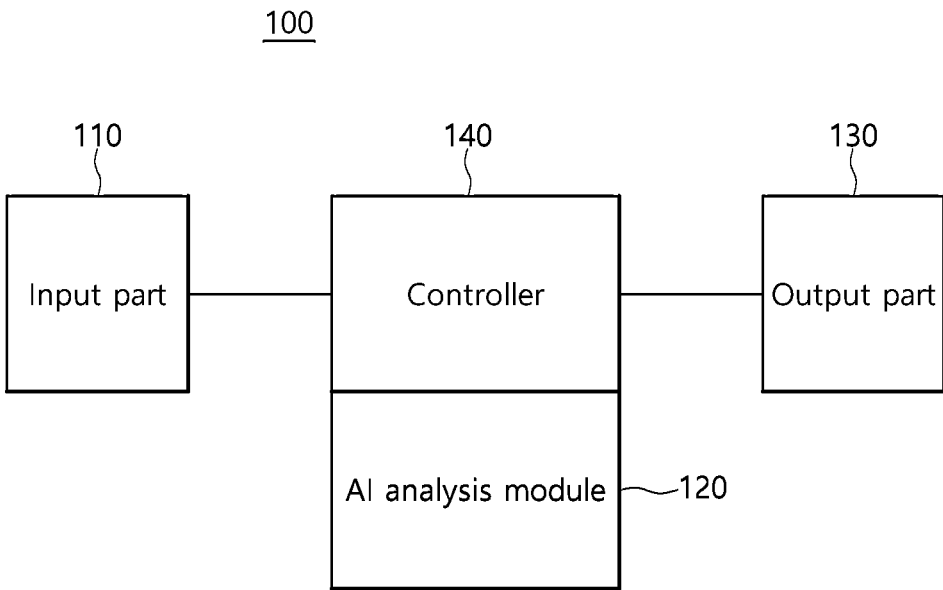
FIG. 1 is a block diagram showing a configuration of a psychological analysis application according to an embodiment of the present invention.

FIG. 1 is a block diagram showing a configuration of a psychological analysis application according to an embodiment of the present invention.

Referring to FIG. 1, a psychological analysis application 100 according to an embodiment of the present invention includes an input part 110, an AI analysis module 120, an output part 130, and a controller 140.

The input part 110 has a screen adapted to receive a doodle or drawing from a user. The input part 110 is a screen of a smartphone or smartpad having a touch screen function. In this case, an input window or electronic sketch screen is activated on the screen of the input part 110 to input the doodle or drawing of the user, and the user's doodle or drawing is inputted to the input window or sketch screen. The doodle or drawing is inputted with the user's finger or stylus pen. According to the embodiment of the present invention, an original image is outputted to the screen and copied by the user to allow the copied doodle or drawing to be inputted to the input part 110. Through the input part 110, the user may add colors to the drawing. According to the embodiment of the present invention, the user's psychological state may be analyzed according to the user's selection of colors inputted.

The controller 140 outputs the original image to the screen of the input part 110 to allow the user to copy the original image. According to the embodiment of the present invention, the psychological analysis application provides a predetermined original image to the screen and analyzes the user's reaction time while he or she is copying the original image, a degree of an overlap between the user's copied drawing and the original image, and the shape of the user's drawing, thereby analyzing the user's psychological state. To do this, the controller 140 outputs various original images to the screen of the input part 110 to allow the user to copy the various original images. The original images provided to the screen of the input part 110 through the controller 140 include simple figures, such as a circle, a square, a triangle, and the like. Further, the original images provided to the screen of the input part 110 are complex paintings such as famous paintings, and the like. The controller 140 may further include a UI through which the user can input colors as well as the drawing to the screen of the input part 110.

The AI analysis module 120 analyzes the user's doodle or drawing inputted to the input part 110 to determine the user's psychological state. The AI analysis module 120 analyzes the user's reaction time while he or she is copying the original image, a degree of an overlap between the user's drawing and the original image, and the shape of the user's drawing to determine the user's psychological state. The AI analysis module 120 includes data that extracts, as features, the user's reaction time while he or she is copying the original image such as a circle, a square, a triangle, an alphabet, and the like, a degree of completion of the user's drawing, and a degree of an overlap between the user's drawing and the original image, and sets scores by sentiment according to the extracted result. Using the data accumulated, the AI analysis module 120 analyzes the user's doodle or drawing inputted to the input part 110 to determine the user's psychological state according to the analyzed result.

The output part 130 outputs the result analyzed in the AI analysis module 120 to the user. The output part 130 includes a screen for outputting image information, and according to the embodiment of the present invention, the screen of the output part 130 may share the screen of the input part 110. That is, the user's psychological state is displayed with a message or picture on the display screen of the user's smartphone or smartpad. The output part 130 further includes a speaker for outputting voice information.

Figure 2:
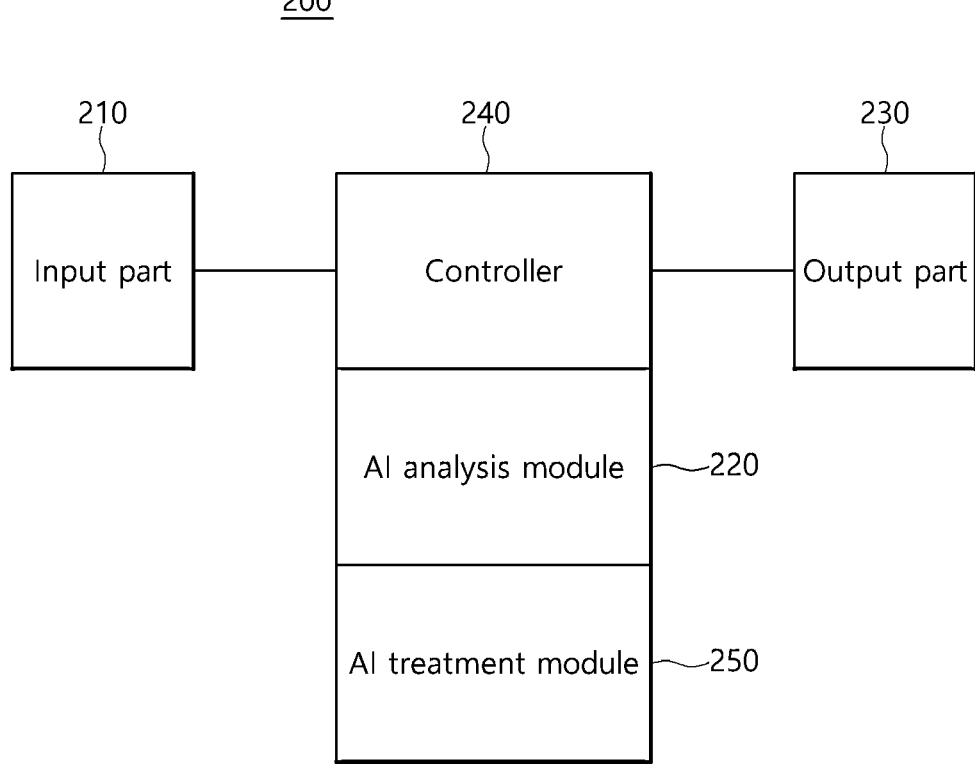
FIG. 2 is a block diagram showing a configuration of a psychological analysis application according to another embodiment of the present invention.

FIG. 2 is a block diagram showing a configuration of a psychological analysis application according to another embodiment of the present invention.

Referring to FIG. 2, a psychological analysis application 200 according to another embodiment of the present invention includes an input part 210, an AI analysis module 220, an output part 230, a controller 240, and an AI treatment module 250.

The input part 210 has a screen adapted to receive a doodle or drawing from a user. The input part 210 is a screen of a smartphone or smartpad having a touch screen function. In this case, an input window or electronic sketch screen is activated on the screen of the input part 210 to input the doodle or drawing of the user, and the user's doodle or drawing is inputted to the input window or sketch screen. The doodle or drawing is inputted with the user's finger or stylus pen. According to the embodiment of the present invention, an original image is outputted to the screen and copied by the user to allow the copied doodle or drawing to be inputted to the input part 210. Through the input part 210, the user may add colors to the drawing. According to the embodiment of the present invention, the user's psychological state may be analyzed according to the user's selection of colors inputted.

The controller 240 outputs the original image to the screen of the input part 210 to allow the user to copy the original image. According to the embodiment of the present invention, the psychological analysis application provides a predetermined original image to the screen and analyzes the user's reaction time while he or she is copying the original image, a degree of an overlap between the user's drawing and the original image, and the shape of the user's drawing, thereby analyzing the user's psychological state. To do this, the controller 240 outputs various original images to the screen of the input part 210 to allow the user to copy the various original images. The original images provided to the screen of the input part 210 through the controller 240 include simple figures, such as a circle, a square, a triangle, and the like. Further, the original images provided to the screen of the input part 110 are complex paintings such as famous paintings, and the like. The controller 240 may further include a UI through which the user may input colors as well as the drawing to the screen of the input part 210.

According to another embodiment of the present invention, the controller 240 outputs the original image to the user's input screen and allows the original image to disappear after a given time. In the case where the user copies the original image in the state where the original image is seen for a short time, the user's drawing copying the position or shape of the original image can be more accurately obtained than that in the case where the user overlappedly copies the original image outputted to the screen. Using the data obtained, the user's psychological state is analyzed through the AI analysis module 220. The controller 240 determines the shape or output time of the original image displayed on the input part 210.

The AI analysis module 220 analyzes the user's doodle or drawing inputted to the input part 210 to determine the user's psychological state. The AI analysis module 220 analyzes the user's reaction time while he or she is copying the original image, a degree of an overlap between the user's drawing and the original image, and the shape of the user's drawing to determine the user's psychological state. The AI analysis module 120 includes data that extracts, as features, the user's reaction time while he or she is copying the original image such as a circle, a square, a triangle, an alphabet, and the like, a degree of completion of the drawing, and a degree of an overlap between the user's drawing and the original image and sets scores by sentiment according to the extracted result. Using the data accumulated, the AI analysis module 220 analyzes the user's doodle or drawing inputted to the input part 110 to determine the user's psychological state according to the analyzed result.

The AI treatment module 250 finds a treatment for the user's psychological state analyzed through the AI analysis module 220. The AI treatment module 250 includes various data of treatments by psychological state. Using such data, the AI treatment module 250 finds the treatment for the user's psychological state analyzed through the AI analysis module 220. For example, if the user's psychological state is 'feel anxious', a treatment for the user's psychological state is provided with a picture, painting, or music making the user feel calm. The AI treatment module 250 pre-builds data of various psychological states and treatments for the various psychological states and finds an appropriate treatment according to situations, time, and the user's age or state.

The output part 230 outputs the result analyzed through the AI analysis module 220 to the user. The output part 230 includes a screen for outputting image information, and according to the embodiment of the present invention, the screen of the output part 230 may share the scree of the input part 210. That is, the user's psychological state is displayed with a message or picture on the display screen of the user's smartphone or smartpad. The output part 230 further includes a speaker for outputting voice information. Further, the output part 230 outputs the treatment for the user's psychological state found through the AI treatment module 250. For example, the output part 230 displays the user's psychological state 'feel anxious' as the result analyzed through the AI analysis module 220 on the screen, and the output part 230 displays 'calm sea picture' as the treatment found through the AI treatment module 250 on the screen or plays relaxing music through the speaker. The operation of the output part 230 is controlled by the controller 240.

Figure 3:
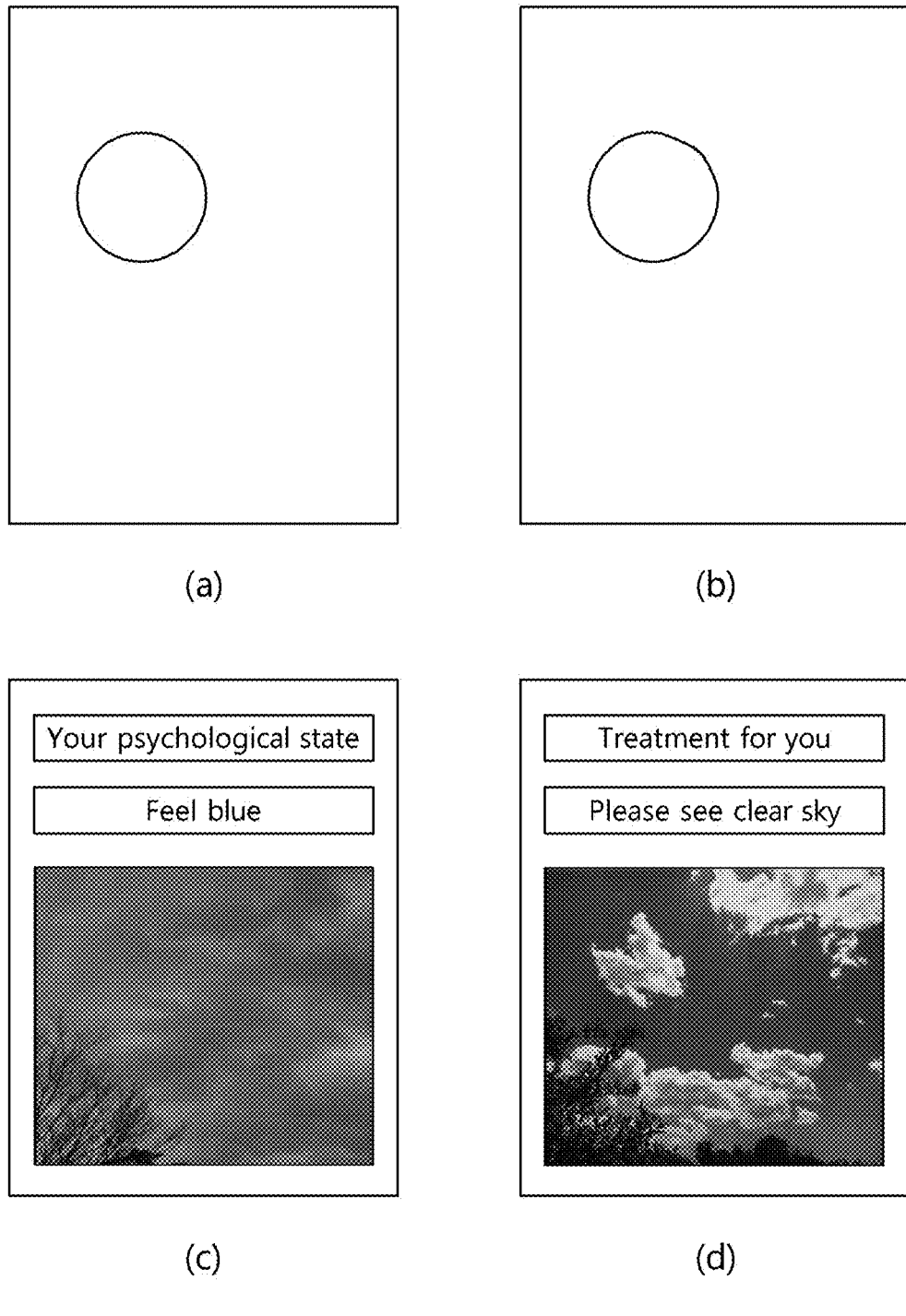
FIG. 3 is a block diagram showing a psychological analysis method according to an embodiment of the present invention.

FIG. 3 is a block diagram showing a psychological analysis method according to an embodiment of the present invention.

Referring to FIG. 3, a psychological analysis method according to the embodiment of the present invention includes the steps of: displaying an original image on a screen (See FIG. 3a), receiving a user's copy of the original image (See FIG. 3b), performing AI analysis for the user's psychological state according to the received user's copy of the original image (not shown), and outputting the user's psychological state analyzed (See FIG. 3c).

FIG. 3a shows the step in which the original image is displayed on the screen to allow the user to input his or her doodle or drawing. A controller outputs the original image to the screen of an input part to allow the user to copy the original image. According to the embodiment of the present invention, the controller outputs various original images to the screen of the input part to allow the user to copy the various original images. The original images provided to the screen of the input part include simple figures, such as a circle, a square, a triangle, and the like. Further, the original images provided to the screen of the input part are complex paintings such as famous paintings, and the like. In this step, the controller may further include a UI through which the user may input colors as well as the drawing to the screen of the input part. In the step where the original image is displayed on the screen, the original image is outputted on the screen of the input part and disappears after a given time.

FIG. 3b shows the step in which the user copies the original image on the screen. This step is performed on the screen of a smartphone or smartpad having a touch screen function. In this case, the drawing is inputted with the user's finger or stylus pen.

The AI analysis step (not shown) is the step in which the user's psychological state is analyzed according to the user's drawing information inputted. In the AI analysis step, the user's reaction time while he or she is copying the original image, a degree of an overlap between the user's drawing and the original image, and the shape of the user's drawing are analyzed to determine the user's psychological state. In the AI analysis step, data is provided to extract, as features, the user's reaction time while he or she is copying the original image, a degree of completion of the drawing, and a degree of an overlap between the user's drawing and the original image, and to set scores by sentiment according to the extracted result. Using the data accumulated, the user's doodle or drawing inputted to the input part is analyzed to determine the user's psychological state according to the analyzed result.

FIG. 3c shows the step in which the user's psychological state analyzed is outputted to the user. In the output step, the analyzed result is outputted to the screen. In the output step, the screen on which the user's psychological state analyzed is outputted may share the screen of the input part. According to the embodiment of the present invention, the user's psychological state is analyzed as 'feel blue', and accordingly, text information for the analyzed result and a rainy image as a background are outputted. That is, the user's psychological state is displayed with a message or picture on the display screen of the user's smartphone or smartpad. In the output step, further, voice information may be outputted through a speaker.

The psychological analysis method according to the embodiment of the present invention further includes the steps of: finding a treatment for the user's psychological state analyzed in the AI analysis step (Not shown) and outputting the treatment found in the AI treatment step (See FIG. 3d).

In the AI treatment step, the treatment for the user's psychological state analyzed in the AI analysis step is found. For example, if the user's psychological state is 'feel blue', the treatment for the user's psychological state is provided with a picture, painting, or music making the user feel excited. In the AI treatment step, data of various psychological states and treatments for the various psychological states is pre-built to find an appropriate treatment according to situations, time, and the user's age or state.

FIG. 3d shows the step in which the treatment the user's psychological state found in the AI treatment step is outputted. For example, if it is displayed that the user's psychological state as the result analyzed in the AI analysis step is 'feel blue' in the step of outputting the user's psychological state, the treatment found in the AI treatment step is outputted with 'a clear sky picture'. In the treatment output step, further, bright cheerful music may be played through the speaker.

Figure 4:
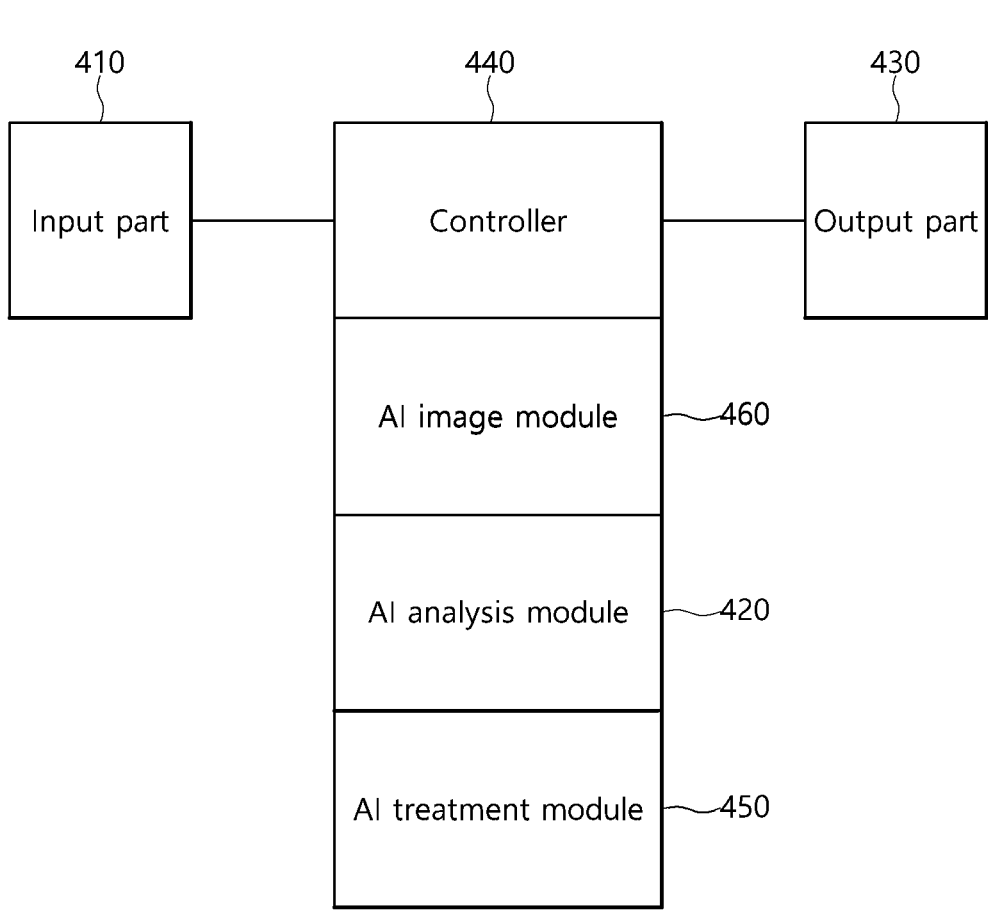
FIG. 4 is a block diagram showing a configuration of a psychological analysis application according to yet another embodiment of the present invention.

FIG. 4 is a block diagram showing a configuration of a psychological analysis application according to yet another embodiment of the present invention.

Referring to FIG. 4, a psychological analysis application 400 according to yet another embodiment of the present invention includes an input part 410, an AI image module 460, an AI analysis module 420, an output part 430, and a controller 440.

The input part 410 has a screen adapted to receive a doodle or drawing from a user. The input part 410 is a screen of a smartphone or smartpad having a touch screen function. In this case, an input window or electronic sketch screen is activated on the screen of the input part 410 to input the doodle or drawing of the user, and the user's doodle or drawing is inputted to the input window or sketch screen. The doodle or drawing is inputted with the user's finger or stylus pen. Through the input part 410, the user may add colors to the drawing. According to the embodiment of the present invention, the user's psychological state may be analyzed according to the user's selection of colors inputted.

The AI image module 460 analyzes the doodle or drawing inputted to the input part 410 and produces a new image based on learned images. The AI image module 460 includes an artificial intelligence picture program such as GauGAN, and the like. The AI image module 460 performs AI analysis for the inputted drawing to produce a realistic image.

The AI analysis 420 module analyzes the user's psychological state according to the shape and color of the new image produced from the AI image module 460. The AI analysis module 420 analyzes the composition, color, and object of the new image to determine the user's psychological state. The AI analysis module 420 includes data of factors analyzing the user's psychological state from the image.

The output part 430 outputs the result analyzed through the AI analysis module 420 to the user. The output part 430 includes a screen for outputting image information, and according to the embodiment of the present invention, the screen of the output part 430 may share the scree of the input part 410. That is, the user's psychological state is displayed with a message or picture on the display screen of the user's smartphone or smartpad. The output part 430 may further include a speaker for outputting voice information.

The controller 440 controls the display screens of the input part 410 and the output part 430. The controller 440 controls the user's input UI displayed on the input part 410 and the output form of the result analyzed through the AI analysis module 420 to the output part 430.

According to the embodiment of the present invention, the AI analysis module 420 further includes an AI treatment module 450. The AI treatment module 450 finds a treatment for the user's psychological state analyzed through the AI analysis module 420. The AI treatment module 450 includes various data of treatments by psychological state. Using such data, the AI treatment module 450 finds the treatment for the user's psychological state analyzed through the AI analysis module 420. For example, if the user's psychological state is 'feel anxious', a treatment for the user's psychological state is provided with a picture, painting, or music making the user feel calm. The AI treatment module 450 pre-builds data of various psychological states and treatments for the various psychological states and finds an appropriate treatment according to situations, time, and the user's age or state.

In this case, the controller 440 allows the treatment found through the AI treatment module 450 to be outputted to the output part 430. For example, the output part 430 displays the user's psychological state 'feel anxious' as the result analyzed through the AI analysis module 420 on the screen, and the output part 430 displays a 'calm sea picture' as the treatment found through the AI treatment module 450 on the screen or plays relaxing music through the speaker. The operation of the output part 430 is controlled by the controller 440.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention. For example, the UI or AI analysis model of the input part and the output part may be freely changed.

The invention claimed is:

1. A psychological analysis system comprising:
an input part having a screen adapted to receive a doodle or drawing from a user;
an AI image module for analyzing the doodle or drawing inputted to the input part to produce a new image based on learned images;
an AI analysis module for analyzing the user's psychological state based on a shape and a color of the new image;
an output part for outputting feedback for the new image produced through the AI image module and the user's psychological state analyzed in the AI analysis module; and
a controller programmed to control displays of the input part and the output part.

2. The psychological analysis system according to claim 1, wherein the AI analysis module further comprises an AI treatment module for finding a treatment for the user's psychological state analyzed therethrough and the controller is programmed to output the treatment found through the AI treatment module to be outputted through the output part.

3. The psychological analysis system according to claim 1, wherein the controller is programmed to output an original image stored in the psychological analysis system, to a screen of the input part to allow the user to copy the original image.

4. The psychological analysis system according to claim 3, wherein the controller is programmed to output the original image to the screen of the input part and allows the original image to disappear after a given time.

5. The psychological analysis system according to claim 3, wherein the AI analysis module is programmed to analyze the user's reaction time while the user is copying the original image, a degree of overlap between an image copied by the user and the original image, and a shape of the image copied by the user.

* * * * *